US012605421B2

(12) United States Patent
    Inui

(10) Patent No.: US 12,605,421 B2
(45) Date of Patent: Apr. 21, 2026

(54) SENESCENCE INHIBITOR

(71) Applicant: SAISEI PHARMA CO., LTD., Osaka (JP)

(72) Inventor: Toshio Inui, Osaka (JP)

(73) Assignee: SAISEI PHARMA CO., LTD., Osaka (JP)

( * ) Notice: Subject to any disclaimer, the term of this patent is extended or adjusted under 35 U.S.C. 154(b) by 0 days.

(21) Appl. No.: 19/082,426

(22) Filed: Mar. 18, 2025

(65) Prior Publication Data

US 2025/0213642 A1     Jul. 3, 2025

Related U.S. Application Data

(63) Continuation of application No. 18/877,761, filed as application No. PCT/JP2023/023139 on Jun. 22, 2023.

(30) Foreign Application Priority Data

Jun. 22, 2022     (JP) ................................. 2022-100488

(51) Int. Cl.
    *A61K 38/01*     (2006.01)
    *A61P 43/00*     (2006.01)
    *C12N 9/38*      (2006.01)
    *C12P 21/06*     (2006.01)

(52) U.S. Cl.
    CPC ............ *A61K 38/018* (2013.01); *A61P 43/00* (2018.01); *C12N 9/2471* (2013.01); *C12P 21/06* (2013.01); *C12Y 302/01023* (2013.01)

(58) Field of Classification Search
    None
    See application file for complete search history.

(56) References Cited

U.S. PATENT DOCUMENTS

| | | |
|---|---|---|
| 2013/0243880 A1 | 9/2013 | Uto et al. |
| 2014/0213522 A1 | 7/2014 | Uto et al. |
| 2015/0152163 A1 | 6/2015 | Uto et al. |
| 2024/0009268 A1 | 1/2024 | Inui |

FOREIGN PATENT DOCUMENTS

| | | |
|---|---|---|
| WO | 2013038997 A1 | 3/2013 |
| WO | 2017176067 A1 | 10/2017 |
| WO | 2022124331 A1 | 6/2022 |

OTHER PUBLICATIONS

Sosa-Diaz et al. "The role of vitamin D on redox regulation and cellular senescence" Free Radical Biology and Medicine 193:253-273. (Year: 2022).*
Zarei et al. "The Relationship Between Vitamin D and Telomere/Telomerase: A Comprehensive Review" The Journal of Frailty and Aging 10:2-9. (Year: 2021).*
Gonzalez-Gualda et al. "A guide to assessing cellular senescence in vitro and in vivo" The FEBS Journal 288:56-80. (Year: 2021).*
Yamamoto et al. "Conversion of vitamin D3 binding protein (group-specific component) to a macrophage activating factor by the stepwise activation of beta-galactosidase of B cells and sialidase of T cells" The Journal of Immunology 151:2794-2802. (Year: 1993).*
Bilke D and Schwartz J "Vitamin D Binding Protein, Total and Free Vitamin D Levels in Different Physiological and Pathophysiological Conditions" Frontiers in Endocrinology 10:317. (Year: 2019).*
Haider T and Husain Q "Hydrolysis of milk/whey lactose by beta galactosidase: A comparative study of stirred batch processes and packed bed reactor prepared with calcium alginate entrapped enzyme" Chemical Engineering and Processing: Process Intensification 48:576-580. (Year: 2009).*
Zarei, M., et al.; "The Relationship Between Vitamin D and Telomere/Telomerase: A Comprehensive Review"; The Journal of Frailty & Aging, vol. 10, No. 1, pp. 2-9; Nov. 1, 2021 (8 pages).
International Search Report issued in corresponding International Application No. PCT/JP2023/023139, mailed Sep. 12, 2023, with translation (7 pages).
Written Opinion issued in corresponding International Application No. PCT/JP2023/023139, mailed Sep. 12, 2023 (3 pages).

* cited by examiner

*Primary Examiner* — Sudhakar Katakam
*Assistant Examiner* — Zachary J Miknis
(74) *Attorney, Agent, or Firm* — Osha Bergman Watanabe & Burton LLP

(57)     ABSTRACT

The present invention aims to provide a senescence inhibitor formed from a material of biological origin. The present invention relates to a senescence inhibitor containing vitamin D-binding protein.

10 Claims, 1 Drawing Sheet

Specification includes a Sequence Listing.

Change in telomere length by intake of MAF capsule

Comparison of telomere length by sex

SEQUENCE LISTING

```
Sequence total quantity: 1
SEQ ID NO: 1            moltype = AA   length = 458
FEATURE                 Location/Qualifiers
source                  1..458
                        mol_type = protein
                        organism = Homo sapiens
SEQUENCE: 1
LERGRDYEKN KVCKEFSHLG KEDFTSLSLV LYSRKFPSGT FEQVSQLVKE VVSLTEACCA   60
EGADPDCYDT RTSALSAKSC ESNSPFPVHP GTAECCTKEG LERKLCMAAL KHQPQEFPTY  120
VEPTNDEICE AFRKDPKEYA NQFMWEYSTN YGQAPLSLLV SYTKSYLSMV GSCCTSASPT  180
```

```
VCFLKERLQL  KHLSLLTTLS  NRVCSQYAAY  GEKKSRLSNL  IKLAQKVPTA  DLEDVLPLAE  240
DITNILSKCC  ESASEDCMAK  ELPEHTVKLC  DNLSTKNSKF  EDCCQEKTAM  DVFVCTYFMP  300
AAQLPELPDV  ELPTNKDVCD  PGNTKVMDKY  TFELSRRTHL  PEVFLSKVLE  PTLKSLGECC  360
DVEDSTTCFN  AKGPLLKKEL  SSFIDKGQEL  CADYSENTFT  EYKKKLAERL  KAKLPDATPT  420
ELAKLVNKHS  DFASNCCSIN  SPPLYCDSEI  DAELKNIL               458
```

SENESCENCE INHIBITOR

The instant application contains a sequence listing in computer readable form (file name: ZAK69WO.xml; date of creation Jun. 2, 2023; file size: 2,371 bytes), which is submitted electronically via EFS-Web in XML format herewith and is hereby incorporated by reference in its entirety.

TECHNICAL FIELD

The present invention relates to a senescence inhibitor.

BACKGROUND ART

Telomere shortening is a cause of cellular senescence. Telomeres are repetitive sequences of 6 bases, TTAGGG, located at the ends of chromosomes and play a role in maintaining the stability of chromosomes and protecting the genetic information. Telomeres shorten with cell division, and this telomere shortening leads to cellular senescence. Senescent cells secrete inflammatory cytokines, leading to afunctional decline of organs and tissues. Thus, telomere shortening is a potential cause of age-related diseases at the whole-body level. Elongating telomeres can potentially inhibit senescence at the whole-body level, but no material of biological origin has been known that can elongate telomeres.

Moreover, vitamin D-binding protein (VDBP), which binds to vitamin D, is a protein contained in plasma and milk and is also referred to as Gc protein. Vitamin D-binding protein is known to have the ability to activate macrophages (Patent Literature 1).

CITATION LIST

Patent Literature

Patent Literature 1: WO2013/038997

SUMMARY OF INVENTION

Technical Problem

The present invention aims to provide a senescence inhibitor formed from a material of biological origin.

Solution to Problem

The present inventors have found that vitamin D-binding protein has a senescence-inhibiting effect, thereby completing the present invention.

Specifically, the present invention relates to a senescence inhibitor, containing vitamin D-binding protein.

Preferably, the vitamin D-binding protein is one treated with one or more enzymes selected from the group consisting of β-galactosidase, sialidase, and N-acetylgalactosaminidase.

Preferably, the vitamin D-binding protein is derived from milk or serum.

Preferably, the milk is colostrum or normal milk.

Preferably, the senescence inhibitor is one for elongating telomeres.

The present invention also relates to a method for producing a senescence inhibitor, the method including bringing vitamin D-binding protein into contact with one or more enzymes selected from the group consisting of β-galactosidase, sialidase, and N-acetylgalactosaminidase.

Advantageous Effects of Invention

The senescence inhibitor of the present invention contains vitamin D-binding protein, which is a material of biological origin, and thus has a low risk of side effects. The senescence inhibitor of the present invention can effectively elongate telomeres of cells.

DESCRIPTION OF EMBODIMENTS

<Vitamin D-Binding Protein>

Figure 1:
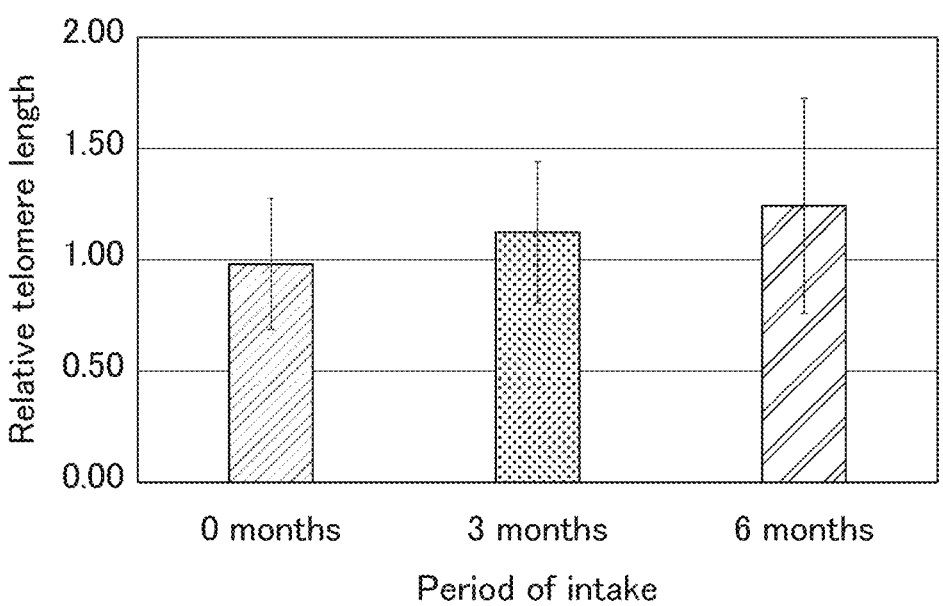
FIG. 1 shows the relative telomere lengths of all subjects.

The senescence inhibitor of the present invention characteristically contains vitamin D-binding protein. The vitamin D-binding protein is a protein present in body fluids such as plasma and milk of mammals, and is also referred to as Gc protein. The vitamin D-binding protein used in the present invention may be any mammal-derived one. Examples include those derived from cattle, goats, mice, and humans, with those derived from cattle being preferred.

Specific examples of the vitamin D-binding protein include polypeptides having at least 85% sequence identity to the amino acid sequence of SEQ ID No: 1 in the Sequence Listing, and polypeptides with an amino acid sequence containing one or more amino acid deletions, insertions, substitutions, and/or additions relative to the amino acid sequence of SEQ ID NO: 1 in the Sequence Listing.

The sequence identity to the amino acid sequence of SEQ ID NO: 1 is preferably at least 90%, more preferably at least 95%, still more preferably at least 988, particularly preferably at least 99%.

The number of amino acid deletions, insertions, substitutions, and/or additions relative to the amino acid sequence of SEQ ID NO: 1 is preferably 68 or less, more preferably 45 or less, still more preferably 22 or less, further preferably 9 or less, particularly preferably 4, 3, 2 or less.

The vitamin D-binding protein to be used may be one contained in a body fluid such as milk or serum of a mammal as described above. Milk, serum, or a treated product thereof containing vitamin D-binding protein may be used as a senescence inhibitor, or purified vitamin D-binding protein may be used as a senescence inhibitor.

The serum may be any of those prepared from blood collected from mammals by any ordinary method. When purifying vitamin D-binding protein from the serum, the purification may be performed, for example, by removing substances such as albumin from the serum, and then adsorbing and eluting vitamin D-binding protein with a vitamin D-binding column, followed by dialysis.

The milk may be colostrum, which is only secreted for a certain number of days after delivery. In particular, bovine colostrum refers to milk secreted by a mother cow within 10 days after delivery. The milk may also be normal milk. Examples of milk components containing vitamin D-binding protein include whey (also referred to as a cheese component-removed component or lactoserum), which is obtained through a cheese component-removing treatment, i.e., a treatment of removing components (e.g., casein and fat) that coagulate into cheese in the production of cheese from milk.

<Gene Recombination>

The vitamin D-binding protein used may be vitamin D-binding protein expressed by gene recombination. The method for expressing vitamin D-binding protein by gene recombination may be performed by culturing host cells transfected with a gene encoding vitamin D-binding protein or by using a cell-free expression system containing a gene encoding vitamin D-binding protein. Examples of the host cells include, but are not limited to, microorganisms of the genera *Streptomyces, Rhodococcus, Escherichia, Bacillus, Pseudomonas, Brevibacterium, Streptococcus, Lactobacillus, Saccharomyces*, and *Kluyveromyces*, as well as cells of higher eukaryotes. Examples of the cells of higher eukaryotes include cells derived from humans, hamsters, chickens, and insects, and examples of specific cell lines include CHO cells, Hela cells, HEK293 cells, sf9 cells, and DT40 cells. Cells may be cultured by either suspension culture or adherent culture, preferably by suspension culture. To avoid contamination with impurities, a serum-free medium is preferably used.

<Enzyme Treatment>

The vitamin D-binding protein may be one treated with one or more enzymes selected from the group consisting of β-galactosidase, sialidase, and N-acetylgalactosaminidase.

Examples of β-galactosidase include those derived from *Escherichia coli* and bovine liver. Examples of commercially available products include catalog no. 072-04141 available from Wako Pure Chemical Industries, Ltd. and G1875 available from Sigma-Aldrich.

β-Galactosidase may be used in any amount and under any treatment conditions, but when a trisaccharide O-glycan composed of N-acetylgalactosamine (GalNAc) linked to sialic acid and galactose is added to the threonine (Thr) at position 418 or 420 of the vitamin D-binding protein used, the conditions are preferably such that this galactose can be dissociated. The temperature of the β-galactosidase treatment is more preferably 35° C. to 39° C. The time of the enzyme treatment is more preferably 60 to 200 minutes. For example, when Catalog No. 072-04141 available from Wako Pure Chemical Industries, Ltd. is used as β-galactosidase, preferably at least 65 mU of the enzyme is used per 100 μl of milk containing vitamin D-binding protein and reacted for three hours or longer. For the activity of β-galactosidase, 1 unit (U) is defined as the amount of the enzyme that produces 1 μmol of o-nitrophenol per minute at pH 7.3 and 37° C. using o-nitrophenol-β-D-galactopyranoside as a substrate.

Examples of sialidase include those derived from *Clostridium perfringenes, Streptococcus* 6646K, *Vibrio cholerae*, and *Arthrobacter ureafaciens*. Examples of commercially available products include product numbers (Sigma Prod. Nos.) N2876, N2133, N2904, N3001, and N5631 available from Sigma-Aldrich, code number 120052 available from Seikagaku Biobusiness, and catalog numbers (catalog #) P0720L and P0720S available from BioLabs.

Sialidase may be used in any amount and under any treatment conditions, but when a trisaccharide O-glycan composed of N-acetylgalactosamine (GalNAc) linked to sialic acid and galactose is added to the threonine (Thr) at position 418 or 420 of the vitamin D-binding protein used, the conditions are preferably such that this sialic acid can be dissociated. The temperature of the sialidase treatment is more preferably 35° C. to 39° C. The time of the enzyme treatment is more preferably 60 to 200 minutes. For example, when product number N2876 available from Sigma-Aldrich is used as sialidase, preferably at least 65 mU of the enzyme is used per 100 μl of milk containing vitamin D-binding protein and reacted for three hours or longer. For the activity of sialidase, 1 unit (U) is defined as the activity that releases 1.0 micromole of N-acetylneuraminic acid per minute at pH 5.0 and 37° C. using mucin from bovine submaxillary glands.

Examples of N-acetylgalactosaminidase include endo-α-N-acetylgalactosaminidase and exo-α-N-acetylgalactosaminidase. Examples of endo-α-N-acetylgalactosaminidase include those derived from *Escherichia coli, Bifidobacterium longum, Streptococcus pneumoniae*, and bovine liver. Examples of commercially available products include catalog #324716 available from Merck.

N-acetylgalactosaminidase may be used in any amount and under any treatment conditions, but when N-acetylgalactosamine (GalNAc) is added to the threonine (Thr) at position 418 or 420 of the vitamin D-binding protein, the conditions are preferably such that this N-acetylgalactosamine can be removed. Endo-α-N-acetylgalactosaminidase is preferably used in an amount of 1 to 500 mU, more preferably 100 to 200 mU, per microgram of vitamin D-binding protein. The temperature of the enzyme treatment is preferably 35° C. to 39° C. The time of the enzyme treatment is preferably 60 to 200 minutes.

For the activity of N-acetylgalactosaminidase, 1 unit (U) is defined as the activity that dissociates 1.0 μmol of p-nitrophenol from p-nitrophenyl-2-acetamido-2-deoxy-3-O-(β-D-galactopyranosyl)-α-D-galactopyranoside in one minute at 37° C. and pH 5.0.

Moreover, when N-acetylgalactosamine is linked to sialic acid, endo-α-N-acetylgalactosaminidase has a reduced effect in cleaving N-acetylgalactosamine, and thus the sialic acid is preferably cleaved beforehand. The sialic acid can be cleaved by subjecting the vitamin D-binding protein to sialidase treatment.

Whether the N-acetylgalactosaminidase treatment has removed N-acetylgalactosamine from the vitamin D-binding protein can be confirmed by the presence or absence of the binding ability to lectins. Examples of the lectins include lectins derived from *Wisteria floribunda* and *Helix pomatia*. If the vitamin D-binding protein does not bind to lectins, it can be determined that N-acetylgalactosamine has been removed.

The enzyme treatment of vitamin D-binding protein may optionally be performed in the presence of a buffer solution. Examples of this buffer solution include saline and phosphate buffered saline (PBS).

The enzyme treatment may be followed by heat treatment to deactivate the enzyme. The heat treatment may be performed under any condition where the enzyme can be inactivated. For example, heating may be performed at a temperature around 60° C. for about 10 minutes. After the enzyme treatment, the enzyme may also be removed from the vitamin D-binding protein by any combination of a vitamin D-binding column, a gel filtration column, ultrafiltration, etc.

The enzyme treatment may also be performed using an enzyme immobilized on a solid phase (immobilized enzyme). The method for immobilizing an enzyme on a solid phase is known to those skilled in the art and may include immobilizing an enzyme on agarose beads with a coupling agent such as cyanogen bromide. Vitamin D-binding protein may be applied to the solid phase on which an enzyme is immobilized to cause an enzyme reaction. The use of such an immobilized enzyme makes it possible to recover the enzyme without deactivating the enzyme by heat treatment after the enzyme treatment, and to remove contaminants (e.g., proteins such as enzymes deactivated by heat treatment).

In the case of enzyme treatment of milk or serum containing vitamin D-binding protein, the enzyme treatment is preferably preceded by a pretreatment. Examples of the pretreatment include concentration to reduce the water content, as well as a treatment of removing components (e.g., casein and fat) that coagulate into cheese in the production of cheese from milk (cheese component-removing treatment). The milk obtained by concentration is referred to as "concentrated milk". The milk obtained by the cheese component-removing treatment is also referred to as cheese component-removed milk, lactoserum, or whey. The vitamin D-binding protein obtained as described above may be further freeze-dried into solid or powder form.

<Senescence Inhibition>

The senescence inhibitor of the present invention can be administered to an individual to inhibit senescence of the individual. Senescence inhibition can be evaluated by measuring the telomere length. The telomere length can be measured, for example, by extracting the chromosomal DNA from cells, causing it to react with a labeled telomere probe, and detecting the emission intensity of the label. If the group of subjects treated with the senescence inhibitor has an extended telomere length compared with the group of subjects not treated with the senescence inhibitor, it can be determined that their senescence is inhibited. The telomere length of the group of subjects treated with the senescence inhibitor is preferably at least 1.02 times, more preferably at least 1.05 times, still more preferably at least 1.1 times, further preferably at least 1.2 times the telomere length of the group of subjects not treated with the senescence inhibitor. The administration of the senescence inhibitor can extend the telomere length regardless of the tissue or cell type. Typical examples of cells include leukocytes, skin cells, and mucosal cells. Leukocytes can be collected from the whole blood, while mucosal cells can be collected from the oral mucosa or nasal cavity.

<Macrophage-Activating Ability>

The vitamin D-binding protein used in the present invention may have a macrophage-activating ability. Vitamin D-binding protein having a macrophage-activating ability may also be referred to as Gc protein-derived macrophage activating factor (GcMAF). Examples of the vitamin D-binding protein having a macrophage-activating ability include vitamin D-binding protein in which no N-acetylgalactosamine (GalNAc) is bound to the threonine (Thr) at position 418 or 420, and vitamin D-binding protein in which GalNAc alone is bound to the threonine (Thr) at position 418 or 420.

The vitamin D-binding protein used in the present invention may also be in the form in which the threonine (Thr) at position 418 or 420 is bound to a trisaccharide 0-glycan composed of N-acetylgalactosamine (GalNAc) linked to sialic acid and galactose. This form is regarded as having no macrophage-activating ability.

The macrophage-activating ability can be evaluated by measuring the phagocytosis ability of macrophages. The phagocytosis ability of macrophages may be measured by adding the vitamin D-binding protein to a culture medium of macrophages, causing the macrophages to phagocytize a test substance such as fluorescent latex beads or zymosan, and calculating the percentage of macrophages that have phagocytized or the number of particles of the test substance phagocytized. If the percentage of macrophages that have phagocytized or the number of particles of the test substance phagocytized is higher/larger than that of the comparative control, it can be determined that there is a macrophage-activating ability. Examples of macrophage cell lines that can be used include RAW264.7, NR8383, and J774.1.

The senescence inhibitor of the present invention may be one that does not increase the production of NO by macrophages. The ability to produce NO can be evaluated by adding the senescence inhibitor to macrophages and measuring the amount of NO produced after the macrophages have been left to stand for about 24 hours. The amount of NO produced can be measured, for example, by the Griess method described in EXAMPLES.

The senescence inhibitor of the present invention may be one that inhibits the production of NO by macrophages. The ability to inhibit NO production can be evaluated by adding the senescence inhibitor and a NO production-stimulating agent such as lipopolysaccharide (LPS) to macrophages and measuring the amount of NO produced after the macrophages have been left to stand for about 24 hours. Inhibition of NO production by macrophages means the presence of an anti-inflammatory effect.

The senescence inhibitor of the present invention may be one that does not increase the production of TNF-$\alpha$ by macrophages. The ability to produce TNF-$\alpha$ can be evaluated by adding the senescence inhibitor, a NO production-stimulating agent such as lipopolysaccharide (LPS), and IFN-$\gamma$ to macrophages and measuring the amount of TNF-$\alpha$ produced after the macrophages have been left to stand for about 24 hours. The amount of TNF-$\alpha$ produced can be measured, for example, by the ELISA method described in EXAMPLES. No increase in TNF-$\alpha$ production by macrophages means the presence of an anti-inflammatory effect.

The senescence inhibitor of the present invention may have an ability to differentiate into M2 macrophages. The ability to differentiate into M2 macrophages can be evaluated by adding the senescence inhibitor to macrophages and measuring the expression level of the marker gene in the macrophages after the macrophages have been left to stand for about 24 hours. The marker gene used may be ARG-1, for example. The expression level of the marker gene can be evaluated, for example, by fluorescence microscopy of immobilized cells, which will be described in EXAMPLES. Commonly known differentiation types of macrophages are proinflammatory M1 and anti-inflammatory M2 macrophages.

<Food Composition>

The senescence inhibitor may optionally be combined with any of various additives usually used for foods, such as auxiliary agents, sweeteners, spices, flavoring agents, antiseptic agents, preservatives, bactericidal agents, and antioxidants, to prepare a food composition.

The food composition may be used as what is called a health food, a health beverage, a functional food, a nutrition function food, a dietary supplement, a nutritional supplementary food (supplement), a food for special dietary uses, a food for specified health uses, or the like. The food composition may be in the form of powder, granules, a tablet such as a sublingual tablet, an enteric-coated capsule, a gastric-coated capsule, an orally disintegrating capsule, a pill, an oral liquid preparation such as suspension, emulsion, syrup, paste, or cream, or other form.

The dose of the food composition may depend on factors such as the age, sex, body weight, and symptoms of the consumer as well as the administration method. In typical examples, the total amount of proteins contained in the food composition is preferably 0.005 to 1.0 mg, more preferably 0.01 to 0.5 mg, still more preferably 0.01 to 0.1 mg, per kilogram of body weight per administration. Moreover, the dose of vitamin D-binding protein is preferably 0.0001 to 1.0 mg, more preferably 0.001 to 0.5 mg, per kilogram of body weight per administration.

When the food composition is administered at the above dose per administration, the dosing interval and the dosing frequency are preferably once a week to three times a day, more preferably twice a week to twice a day, still more preferably once or twice a day. The administration is preferably continued for one month or longer, more preferably two months or longer, still more preferably three months or longer, further preferably four months or longer, particularly preferably six months or longer.

<Pharmaceutical Composition>

The senescence inhibitor may optionally be combined with a pharmaceutically acceptable additive to prepare a pharmaceutical composition. Examples of such pharmaceutically acceptable additives include diluents, stabilizers, preservatives, and buffers.

The pharmaceutical composition may be in any form, such as an injectable composition, an oral composition, an ophthalmic composition, an infusion composition, a nasal composition, an ear composition, a suppository, an enteral nutritional composition, etc. The oral composition may be in the form of powder, granules, a tablet such as a sublingual tablet, a capsule, a pill, an enteric-coated capsule, an oral liquid preparation such as suspension, emulsion, or syrup, an inhalation, or other form. Examples of the injection form include intravenous injection, subcutaneous injection, intradermal injection, intramuscular injection, and intraperitoneal injection.

The dose of the pharmaceutical composition may depend on factors such as the age, sex, body weight, and symptoms of the patient as well as the administration method. In typical examples, the total amount of proteins contained in the pharmaceutical composition is preferably 0.005 to 1.0 mg, more preferably 0.01 to 0.5 mg, still more preferably 0.01 to 0.1 mg, per kilogram of body weight per administration. Moreover, the dose of vitamin D-binding protein is preferably 0.0001 to 1.0 mg, more preferably 0.001 to 0.5 mg, per kilogram of body weight per administration.

When the pharmaceutical composition is administered at the above dose per administration, the dosing interval and the dosing frequency are preferably once a week to three times a day, more preferably twice a week to twice a day, still more preferably once or twice a day. The administration is preferably continued for one month or longer, more preferably two months or longer, still more preferably three months or longer, further preferably four months or longer, particularly preferably six months or longer.

<Indications>

Since the vitamin D-binding protein can have a macrophage-activating ability, the pharmaceutical composition of the present invention may have, in addition to the senescence-inhibiting effect, a disease treatment effect based on macrophage activation. Examples of such diseases include cancers, infectious diseases, autoimmune diseases, autism, inflammatory diseases, brain and neurodegenerative diseases, dermatological diseases, and heart diseases.

The cancers include all carcinomas, sarcomas, and other malignant tumors. Examples include skin cancer, bronchial cancer, lung cancer, non-small cell lung cancer, breast cancer, ovarian cancer, tongue cancer, pharyngeal cancer, esophageal cancer, stomach cancer, small intestine cancer, colorectal cancer, rectal cancer, colon cancer, liver cancer, pancreatic cancer, kidney cancer, renal cell carcinoma, bladder cancer, prostate cancer, uterine cancer, cervical cancer, Wilms' tumor, malignant melanoma, meningioma, neuroblastoma, osteosarcoma, Kaposi's sarcoma, lymphoma, and leukemia. In addition to these malignant tumors, the cancers also include metastases thereof.

Examples of the infectious diseases include viral infectious diseases and bacterial infectious diseases, specifically novel coronavirus infection (COVID-19), HIV infection, and AIDS, as well as hepatitis B, hepatitis C, herpes, influenza, pneumonia, tuberculosis, and EB virus infection.

The autism is a behavioral disorder characterized by difficulties in forming social relationships with others, delayed language development, etc.

The inflammatory diseases are diseases arising from inflammation, which is part of the body's defense response to physical stimuli, chemical stimuli, and microbial infections. The pharmaceutical composition of the present invention is also effective against autoinflammatory diseases in which an inflammatory response occurs spontaneously due to abnormal innate immunity, leading to organ damage.

Examples of the brain and neurodegenerative diseases include Alzheimer's disease, Parkinson's disease, spinocerebellar degeneration, amyotrophic lateral sclerosis, and Lewy body dementia.

Examples of skin improvements include skin whitening, suppression or amelioration of pigmentation, exfoliation and promotion of keratin turnover, anti-aging, suppression or amelioration of wrinkles, moisturizing, regeneration, and treatment or prevention of alopecia.

Examples of the heart diseases include congestive heart failure, arrhythmia, angina pectoris, and myocardial infarction.

<Quasi-Drug Composition>

The senescence inhibitor may optionally be combined with an auxiliary agent or the like to prepare a quasi-drug composition. The quasi-drug composition can be in any of various forms such as solution, suspension, syrup, granules, cream, paste, and jelly, and may also be formed into a desired shape as required. The quasi-drug composition in any form can be produced by an ordinary method.

The amount of Gc protein used in the quasi-drug composition may be, but is not limited to, the same as the dose for the pharmaceutical composition, or may be set as appropriate with reference to the above dose.

<Method for Producing Senescence Inhibitor>

The method for producing a senescence inhibitor according to the present invention characteristically includes bringing vitamin D-binding protein into contact with one or more enzymes selected from the group consisting of β-galactosidase, sialidase, and N-acetylgalactosaminidase. The β-galactosidase, sialidase, N-acetylgalactosaminidase, and enzyme treatment conditions are as described above with respect to the senescence inhibitor.

When sialidase and N-acetylgalactosaminidase are used in the method for producing a senescence inhibitor of the present invention, preferably, vitamin D-binding protein is first treated with sialidase and then with N-acetylgalactosaminidase. This is because, when sialic acid is bound to the vitamin D-binding protein via N-acetylgalactosamine, N-acetylgalactosaminidase has a reduced efficiency in cleaving N-acetylgalactosamine. Cleaving sialic acid beforehand can improve efficiency in cleaving N-acetylgalactosamine.

EXAMPLES

(1) Production of Capsules Containing Vitamin D-Binding Protein (Production Example 1)

Crude cheese component-removed milk obtained by cheese component-removing treatment (lactoserum obtained from General Incorporated Foundation Zao Dairy Center) was centrifuged at 8000 rpm and 4° C. for one hour, and the supernatant was collected while taking care of the precipitate. An equal amount of distilled water (Mill-Q grade; hereinafter, distilled water of the same grade was used unless otherwise specified) was added to the collected supernatant, followed by dialysis treatment through a pencil-type module UF membrane (AIP-0013D, Funakoshi Co., Ltd.). At this time, the dialysis was performed until the amount of filtrate equaled the amount of distilled water added, thereby obtaining cheese component-removed milk (lactoserum). The protein concentration was determined by absorbance measurement at a wavelength of 570 nm (using a calibration curve prepared with bovine serum albumin (BSA, A4503, Sigma).

The cheese component-removed milk obtained above was dispensed to have a protein content of 6 g. To this cheese component-removed milk, 4 g/6000 U of β-galactosidase (derived from *Escherichia coli*, Oriental Yeast Co., Ltd.) immobilized with a formyl resin (Formy-650M, Toyopearl) was added, and the mixture was incubated at 37° C. for one hour. After the incubation, the reaction liquid was filtered through a glass filter to separate the formyl resin. The formyl resin was washed with distilled water and stored for repeated use. The filtrate was filter-sterilized with Labodisc (50CP020AS, Advantec Toyo Kaisha, Ltd.). The sterilized filtrate was freeze-dried and powdered to obtain an enzyme-treated milk powder. The presence of vitamin D-binding protein in the enzyme-treated milk was confirmed by Western blotting as described in WO 2016/194914 using an anti-vitamin D-binding protein antibody.

(2) Test for Administration of Capsules Containing Vitamin D-Binding Protein (Working Example)

The enzyme-treated milk prepared above was used to prepare enteric-coated capsules by an ordinary method in which the amount of proteins was adjusted to 1.0 mg. The enteric-coated capsules were orally administered daily to 167 healthy subjects (118 females and 49 males), twice a day in the morning and evening, with one capsule per administration, i.e., two capsules per day.

Here, the age composition of the subjects was as follows: 60 subjects in their 40s; 52 subjects in their 50s; 28 subjects in their 60s; 24 subjects in their 70s; 2 subjects in their 80s; and 1 subject in their 90s.

Blood samples were collected from the subjects at the start of the administration test and at 3 and 6 months after the start of the administration test. Chromosomal DNA was extracted from the blood cells and the telomere length was measured by real-time qPCR as described in the following article. The average telomere length of all subjects was then calculated.

Journal of Affective Disorders 273 (2020) 453-461, Zeyue Liu et al., "Inverse changes in telomere length between the blood and brain in depressive-like mice"

FIG. 1 shows the relative telomere lengths at the start of the administration test and at 3 and 6 months after the start of the administration test. At 3 and 6 months after the start of the administration test, the relative telomere length was increased according to the administration period. A significant difference of $p<0.01$ was found between the relative telomere lengths at the start of administration and after 3-months administration, between those at the start of administration and after 6-months administration, and between those after 3-months administration and after 6-months administration.

Figure 2:
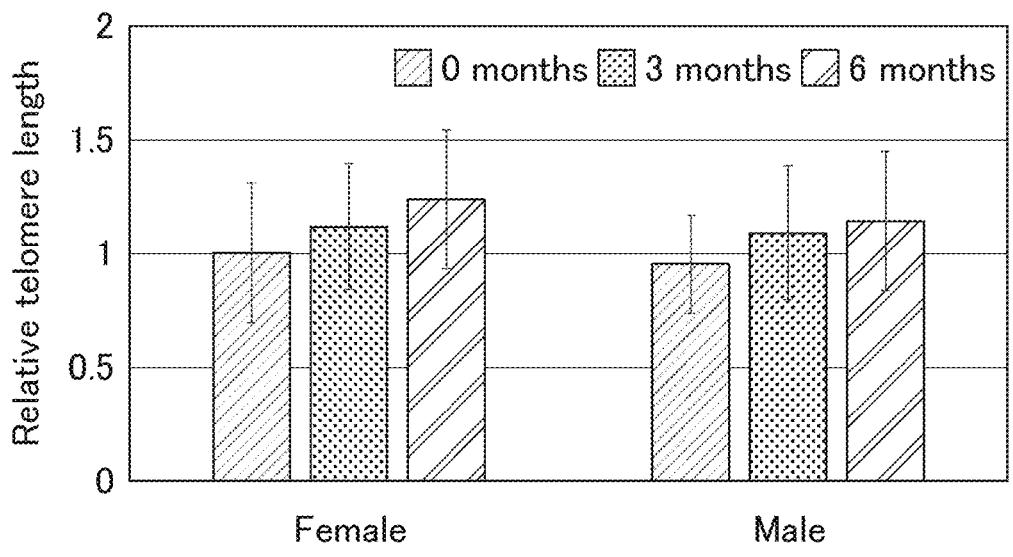
FIG. 2 shows the relative telomere lengths of the subjects by sex.

Moreover, FIG. 2 shows the telomere lengths of the subjects by sex. At 3 and 6 months after the start of the administration test, the relative telomere length was increased for both males and females according to the administration period. For the females, a significant difference of $p<0.01$ was found between the relative telomere lengths at the start of administration and after 3-months administration and between those after 3-months administration and after 6-months administration. Also, for the males, a significant difference of $p<0.01$ was found between the relative telomere lengths at the start of administration and after 3-months administration. It should be noted that no significant difference in telomere length was observed between the males and females, demonstrating that the senescence inhibitor of the present invention is effective regardless of sex.

Embodiment 1 of the present disclosure relates to a senescence inhibitor, containing vitamin D-binding protein.

Embodiment 2 of the present disclosure relates to the senescence inhibitor according to Embodiment 1 of the present disclosure, wherein the vitamin D-binding protein is one treated with one or more enzymes selected from the group consisting of β-galactosidase, sialidase, and N-acetyl-galactosaminidase.

Embodiment 3 of the present disclosure relates to the senescence inhibitor according to Embodiment 1 or 2 of the present disclosure, wherein the vitamin D-binding protein is derived from milk or serum.

Embodiment 4 of the present disclosure relates to the senescence inhibitor according to Embodiment 3 of the present disclosure, wherein the milk is colostrum or normal milk.

Embodiment 5 of the present disclosure relates to the senescence inhibitor according to any one of Embodiments 1 to 4 of the present disclosure, for elongating telomeres.

Embodiment 6 of the present disclosure relates to a method for producing a senescence inhibitor, the method including bringing vitamin D-binding protein into contact with one or more enzymes selected from the group consisting of β-galactosidase, sialidase, and N-acetylgalactosaminidase.

---

The invention claimed is:

1. A method for elongating telomeres in blood cells of a subject, comprising administering cheese component-removed milk to the subject, wherein the cheese component-removed milk is one treated with β-galactosidase.

2. The method according to claim 1, wherein the cheese component-removed milk is one further treated with one or more enzymes selected from the group consisting of sialidase and N-acetylgalactosaminidase.

3. The method according to claim 1, wherein the cheese component-removed milk comprises vitamin D-binding-protein.

4. The method according to claim 1, wherein the cheese component-removed milk is obtained by subjecting colostrum or normal milk to a cheese component-removing treatment.

5. The method according to claim 1, wherein the administration is an oral administration.

6. A method for elongating telomeres in blood cells of a subject, comprising:

bringing cheese component-removed milk into contact with β-galactosidase, and administering the cheese component-removed milk to the subject.

7. The method according to claim 6, wherein the administration is an oral administration.

8. The method according to claim 6, wherein the cheese component-removed milk comprises vitamin D-binding protein.

9. The method according to claim 1, wherein the blood cells are leukocytes.

10. The method according to claim 6, wherein the blood cells are leukocytes.

* * * * *